United States Patent
Tyrell et al.

(10) Patent No.: US 9,587,130 B2
(45) Date of Patent: Mar. 7, 2017

(54) ANTI-KOGATION AGENTS

(75) Inventors: Paul Tyrell, Corvallis, OR (US);
Robert A. Brunck, Corvallis, OR (US);
Kevin P. DeKam, Corvallis, OR (US);
Garry Hinch, Vancouver, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 543 days.

(21) Appl. No.: 13/825,756

(22) PCT Filed: Sep. 24, 2010

(86) PCT No.: PCT/US2010/050306
§ 371 (c)(1),
(2), (4) Date: Mar. 22, 2013

(87) PCT Pub. No.: WO2012/039721
PCT Pub. Date: Mar. 29, 2012

(65) Prior Publication Data
US 2013/0194364 A1    Aug. 1, 2013

(51) Int. Cl.
*C09D 11/38* (2014.01)
*C07F 9/09* (2006.01)
*C09D 11/322* (2014.01)

(52) U.S. Cl.
CPC .............. *C09D 11/38* (2013.01); *C07F 9/091* (2013.01); *C09D 11/322* (2013.01)

(58) Field of Classification Search
CPC ........ C07F 9/091; C09D 11/38; C09D 11/322
USPC ..................... 106/31.59, 31.89, 31.58, 31.86
See application file for complete search history.

(56) References Cited

U.S. PATENT DOCUMENTS

| | | | |
|---|---|---|---|
| 4,153,482 A | 5/1979 | Stayner et al. | |
| 5,062,892 A | 11/1991 | Halko | |
| 5,720,800 A | 2/1998 | Matsumoto | |
| 6,069,210 A | 5/2000 | Cartridge et al. | |
| 6,592,657 B2 | 7/2003 | Lee et al. | |
| 7,388,040 B2 | 6/2008 | Sader et al. | |
| 7,524,800 B2 | 4/2009 | Futterer | |
| 2005/0225615 A1* | 10/2005 | Sader et al. ................... 347/95 |
| 2005/0256226 A1 | 11/2005 | Thetford et al. | |
| 2008/0200588 A1 | 8/2008 | Fenn et al. | |
| 2011/0271870 A1* | 11/2011 | Otsubo et al. ............. 106/31.13 |

FOREIGN PATENT DOCUMENTS

| | | |
|---|---|---|
| CN | 1930246 | 3/2007 |
| JP | 1986102295 | 5/1986 |
| JP | 61118291 | 6/1986 |
| JP | H08209048 | 8/1996 |
| JP | 2001072692 | 3/2001 |
| JP | 2002256141 | 9/2002 |
| JP | 2002309039 A * | 10/2002 |
| JP | 2003055590 | 2/2003 |
| JP | 2005297564 | 10/2005 |
| JP | 2010095680 | 4/2010 |
| WO | 2009078833 | 6/2009 |

OTHER PUBLICATIONS

Croda, Phosphate Ester, Year 2009, pp. 1-4.*
Groves et al., Phase studies of mixed phosphated surfactants, n-hexane and water, J. Pharm. Pharmac., 1974, 26, 616-623.
Misra et al., Lubrication studies of aqueous mixtures of inversely soluble components, Colloids and Surfaces, A: Physiochemical and Engineering Aspects 170 (2000), 91-106.
Anonymous, Oleth-5 Phosphate, url:http://ww.specialchem4cosmetics.com/services/inci/ingredient.aspx?id=8415, retrieved on May 29, 2013.
Supplementary European Search Report dated Feb. 7, 2013, Reference 201000398EP01, Application No./Patent No. 10857617.4-1462 PCT/US2010050306; Hewlett-Packard Development Company, L.P.

* cited by examiner

*Primary Examiner* — Veronica F Faison
(74) *Attorney, Agent, or Firm* — HP Inc. Patent Department

(57) ABSTRACT

Anti-kogation agents and ink compositions containing it. Such anti-kogation agent has the formula (I) or (II) wherein R is an alkyl group having from 1 to 10 carbon atoms and n is an integer ranging from 3 to 10. A disclosed ink composition includes an ink vehicle, from about 0.1 to about 10 weight percentage of colorants and from about 0.01 to about 10 weight percentage of the anti-kogation agents.

12 Claims, No Drawings

ANTI-KOGATION AGENTS

BACKGROUND

The use of inkjet printing systems has grown dramatically in recent years, this use is attributed to substantial improvements in print resolution and overall print quality coupled with appreciable reduction in cost. Notwithstanding their recent success, intensive research and development efforts continue toward improving inkjet print quality, while further lowering cost to the consumer.

With inkjet printing, a desired printed image is formed when a precise pattern of dots is ejected from a drop-generating device, known as a printhead, onto a print medium. The printhead has an array of precisely formed nozzles located on a nozzle plate and attached to an inkjet printhead substrate. The inkjet printhead substrate incorporates an array of firing chambers that receive inkjet ink through fluid communication with one or more ink reservoirs. Each firing chamber has a resistor element, known as a firing resistor, located opposite the nozzle. Upon energizing of the resistor element, a droplet of inkjet ink is expelled through the nozzle toward the print medium. The small scales of the nozzles, which are about 10 μm to 40 μm in diameter, require that the ink does not clog the nozzles. However, repeated firings of the resistor elements, which are designed to withstand millions of firings over the life of the print cartridge, result in fouling of the resistor elements with residue. The term "kogation" is used herein to refer to the buildup of the residue, or koga, on a surface of the resistor element.

Therefore, to produce high quality images, the inkjet ink has to be capable of passing through the inkjet orifice without clogging the orifice plate.

Inkjet ink often includes one or more colorants dissolved or dispersed in an aqueous-based ink vehicle and can also contain anti-kogation agents. Such anti-kogation agents have been used to counter the kogation effect. However, such agents tend to be not stable in the ink composition and often precipitate. Such precipitation phenomenon results in a deposition phenomenon which tend to clog the nozzles. Such clogging happens at the fore end of the nozzle so that the direction and quantity of ink jetted become unstable. This phenomena result in poor printing performances. This clogging phenomenon is, furthermore, accentuated when metal ions contaminate ink composition.

It has thus often created challenges to formulate ink compositions that do not have kogation effect and that do not result in clogging the nozzle of the printing machine; in other words, that can be effectively used with inkjet printing techniques and that provide good image printing performances.

DETAILED DESCRIPTION

Before embodiments of the present disclosure are described in detail, it is to be understood that, unless otherwise indicated, the present disclosure is not limited to particular materials, and processes disclosed herein as such may vary to some degree. It is also to be understood that the terminology used herein is for purposes of describing particular embodiments only, and is not intended to be limiting, as the scope of the present invention will be defined only by the claims and equivalents thereof. In describing and claiming the present exemplary composition and method, the following terminology will be used: the singular forms "a", "an", and "the" include plural referents unless the context clearly dictates otherwise. Thus, for example, reference to "a pigment" includes reference to one or more of such materials. Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of approximately 1 wt % to about 20 wt % should be interpreted to include not only the explicitly recited concentration limits of 1 wt % to about 20 wt %, but also to include individual concentrations such as 2 wt %, 3 wt %, 4 wt %, and sub-ranges such as 5 wt % to 15 wt %, 10 wt % to 20 wt %, etc. Wt % means herein percentage by weight. All percents are by weight unless otherwise indicated. Standard temperature and pressure are defined as 20° C. and 1 atmosphere. Unless indicated otherwise, the viscosity is expressed in cP and is measured at a temperature of 25° C.

In some embodiments, the present disclosure refers to anti-kogation agents having the formula (I) or (II):

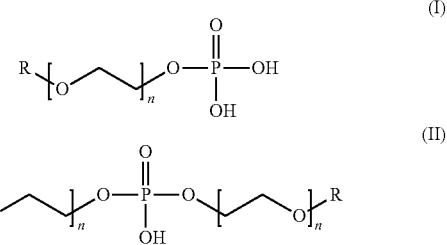

wherein R is an alkyl group having from 1 to 10 carbon atoms and n is an integer ranging from 3 to 10. In some examples, the anti-kogation agents designate a mixture of mono-ester and di-ester having the formula (I) and/or the formula (II) such as described above.

In some other embodiments, the present disclosure refers to ink composition containing an ink vehicle, from about 0.1 to about 10 weight percentage of colorants and from about 0.01 to about 10 weight percentage of anti-kogation agents that are a mixture of mono-ester and di-ester having the formula (I) and/or the formula (II):

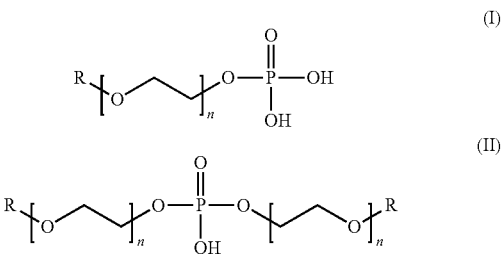

wherein R is an alkyl group having from 1 to 10 carbon atoms and n is an integer ranging from 3 to 10.

Ink compositions containing anti-kogation agents, such as defined herein, reduce kogation phenomenon and clogging phenomenon that can happen in internal ink channels, in firing chambers or in nozzles. Such compositions have also a good affect on the filterability of the ink Ink compositions containing said anti-kogation agents offer then a means to avoid filterability issues and/or potential nozzle clogging issues while still having good anti-kogation performances.

The use of anti-kogation agents, as described herein, avoid kogation troubles without suffering from clogging troubles. Indeed, without being linked by any theory, it is believed that anti-kogation agents do not react with metal ions and thus do not create insoluble salts that precipitate and load the filters present in the printhead, and ultimately clog the flow of ink to the nozzles Ink compositions, containing such anti-kogation agents, present therefore good anti-kogation property in combination with good anti-clogging properties.

Furthermore, ink compositions containing anti-kogation agents such as described herein have improved printing characteristics. Indeed, kogation and clogging problems tend to reduce drop velocity and drop weight and reduce efficiency of drop ejection. A loss of drop weight over the life of the inkjet pen reduces the accuracy of drop placement and reduces the optical density of the ink on the print medium and, therefore, degrades print quality.

As anti-kogation agents, it is meant herein any components that prevent or reduce the kogation effect. In some embodiments, the anti-kogation agents have the formula (I) or the formula (II):

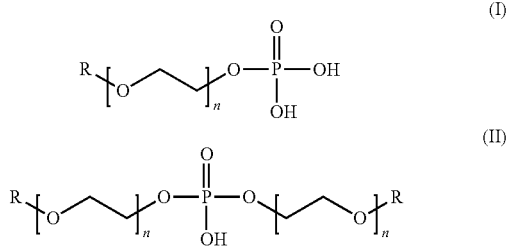

wherein R is an alkyl group having from 1 to 10 carbon atoms and n is an integer ranging from 3 to 10. As used herein, n represents the number of ethoxylation groups present in formula (I) and in both ester substituents in formula (II). In some examples, the anti-kogation components is a mixture of mono-ester and di-ester having the formula (I) and/or the formula (II) such as defined herein.

The anti-kogation components can be a mixture of mono-ester anti-kogation agent of formula (I) and of di-ester anti-kogation agent of formula (II), such as defined herein, wherein the anti-kogation agent of formula (I) represents up to 100% of the mixture. In some examples, the anti-kogation agent of formula (I) represents up to 90% of the mixture. In some other examples, the anti-kogation agent of formula (I) represents up to 80% of the mixture and, in yet some other examples, the anti-kogation agent of formula (I) represents up to 70% of the mixture.

Thus, in some other embodiments, the anti-kogation agent is a mono-ester having the formula (I):

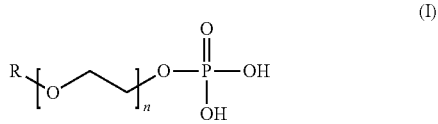

wherein R is an alkyl group having from 1 to 10 carbon atoms and n is an integer ranging from 3 to 10.

In formula (I) and/or (II), R can be a linear or a branched alkyl group. R can be a linear alkyl group, each group containing from 1 to 10 carbon atoms. In some examples, R is a linear alkyl group, each group containing from 1 to 8 carbon atoms. In some other examples, R is a linear substituted or unsubstituted alkyl group. In yet some other examples, R is a linear unsubstituted alkyl group. In the formula (I) and/or (II), R can be a linear alkyl group having 1, 2, 3 or 4 carbons atoms. In some examples, R is a liner alkyl group having 4 carbon atoms. In some other examples, R is —(CH$_2$)$_3$CH$_3$.

In the formula (I) and/or (II), n can be an integer ranging from 3 to 10 or from 3 to 7. In some examples, n is 3 or 4, meaning thus that the anti-kogation agent contains a hydrophobic tail including 3 or 4 ethoxylated groups. In some other examples, n is 3, meaning thus that the anti-kogation agent contains a hydrophobic tail including 3 ethoxylated groups.

In some examples, the anti-kogation agent is a mixture of mono-ester and di-ester having the formula (I) and/or the formula (II) wherein R is a liner alkyl group having 4 carbon atoms and wherein n is 3. In some other examples, the anti-kogation agent is a mixture of mono-ester and di-ester having the formula (I) and/or the formula (II) wherein R is —(CH$_2$)$_3$CH$_3$ or —CH$_2$—CH$_3$ and wherein n is 3. In some yet other examples, the anti-kogation agent has the formula (I) wherein R is —(CH$_2$)$_3$CH$_3$ and wherein n is 3. Meaning thus that the anti-kogation agent has the formula:

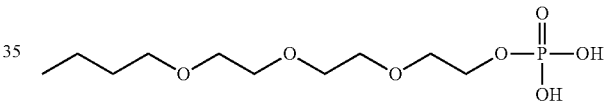

The anti-kogation agents can also be a mixture of pure short alkyl chain with tri or tetra ethoxy phosphate esters. In some examples, the anti-kogation agents are alkyl ether esters of phosphate.

The anti-kogation agents can be synthesized by the use of pure solvents such as triethylene glycol mono methyl ether, triethylene glycol mono ethyl ether, triethylene glycol mono butyl ether, and tetraethylene glycol mono methyl ether. Such pure solvent can then be mixed with poly-phosphoric acid or phosphoryl chloride (POCl$_3$). In some examples, such process can result in pure single oligomer components rather than a mixture of poly-ethoxylated oligomers. In some examples, a method to produce anti-kogation agents having the formula (I) and/or the formula (II), such as defined herein, includes reacting at least a pure solvent selected from the group consisting of triethylene glycol mono methyl ether, triethylene glycol mono ethyl ether, triethylene glycol mono butyl ether, tetraethylene glycol mono methyl ether with poly-phosphoric acid or phosphoryl chloride (POCl$_3$).

The anti-kogation agents, such as described herein, can be used in ink composition. In some examples, the ink composition is an inkjet ink printing composition. By inkjet composition, it is meant herein that the composition is very well adapted to be used in an inkjet device and/or in an inkjet printing process.

In some examples, the ink composition contains an ink vehicle, from about 0.1 to about 10 weight percentage of colorants, and from about 0.01 to about 10 weight percentage of anti-kogation agents, said anti-kogation agent being a mixture of mono-ester and di-ester having the formula (I) and/or the formula (II):

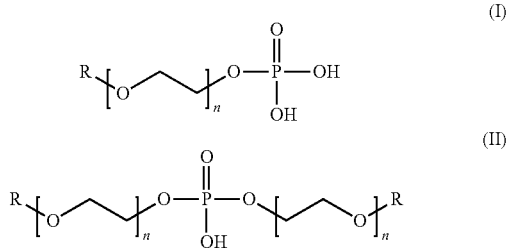

wherein R is an alkyl group having from 1 to 10 carbon atoms and n is an integer ranging from 3 to 10.

In some other examples, the ink composition contains an ink vehicle, from about 0.1 to about 10 weight percentage of colorants, and from about 0.01 to about 10 weight percentage of an anti-kogation agent having the formula (I):

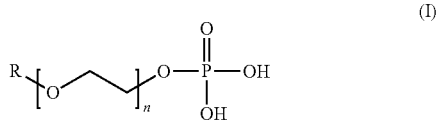

wherein R is an alkyl group having from 1 to 10 carbon atoms and n is an integer ranging from 3 to 10. In yet some other examples, the ink composition contains an ink vehicle, from about 0.1 to about 10 weight percentage of colorants, and from about 0.01 to about 10 weight percentage of anti-kogation agents having formula (I) wherein R is —$(CH_2)_3CH_3$ and wherein n is 3.

The anti-kogation agent can be present, in the ink composition, in an amount representing from about 0.01 to about 10 weight percentage (wt %) of the total weight of the ink composition. In some examples, the anti-kogation agent is present in an amount representing from about 0.2 to about 3 weight percentage. In some other examples, the anti-kogation agent is present in an amount representing from about 0.4 to about 1 weight percentage of the total weight of the ink composition.

The pH of the ink may be in the range of about 3 to about 11, depending on the type of colorant being used. In some examples, the pH of the present ink is from about 5 to about 9 and, in some other examples, from about 5.5 to about 7.5. The pH of the ink composition may be adjusted by addition of organic or inorganic acids or bases, i.e. pH adjusting agent. Such pH adjusting agent includes inorganic acids such as hydrochloric, phosphoric and sulfuric acids. Organic acids include, but are not limited to methane sulfonic, acetic and lactic acids. Inorganic bases include but are not limited to alkali metal hydroxides and carbonates. In some examples, pH adjusting agent is ammonium hydroxide. The pH adjusting agent can be used in an amount representing from about 0.1 to about 1 percentage by weight, or can be used in an amount representing from about 0.3 to about 0.7 percentage by weight of the composition.

The ink composition can have a viscosity within the range of about 1.0 to about 10 cps, or within the range of about of about 1.0 to about 7.0 cps, as measured at 25° C., in order to achieve the desired rheological characteristics. The viscosity of the ink composition is conveniently regulated, as known to those of ordinary skill in the art, for instance, by suitable choice of the quantity and the molecular weight of the organic solvent, wax or other agents.

The ink composition includes one or more colorants that impart the desired color to the printed message. As used herein, "colorant" includes dyes, pigments, and/or other particulates that may be suspended or dissolved in an ink vehicle. The colorant system can be present in an amount ranging from about 0.1 to about 10 percentage by weight (wt %) or in an amount ranging from about 1 to about 6 percentage by weight. In some examples, the colorant system is present in an amount ranging from about 1 to about 4 percentage by weight of the ink composition.

The ink can contain pigments as colorants. As used herein, "pigment" refers to a colorant particle that is substantially insoluble in the liquid vehicle in which it is used. Pigments can be dispersed using a separate dispersing agent, or can be self-dispersed, having a dispersing agent attached to the surface of the pigment. As used herein, "self-dispersed" refers to pigments that have been functionalized with a dispersing agent, such as by chemical attachment of the dispersing agent to the surface of the pigment. The dispersing agent can be a small molecule or a polymer or oligomer. The dispersing agent can be attached to such pigments to terminate the outer shell of the pigment with a charge, thereby creating a repulsive nature that reduces agglomeration of pigment particles within the liquid vehicle. Another way to disperse carbon black is to surface treat the carbon (with ozone, as an example) to create charged functional groups on the surface of the carbon itself. Pigments that can be used include both self-dispersed pigments as well as dispersed pigments, e.g., pigments dispersed by a separate dispersing agent that is not covalently attached to the surface. If self-dispersed, a dispersant is typically prepared in a precursor form, and then the precursor is attached to the pigment to chemically modify the surface of the pigment. Dispersant can also be attached to the pigment using various precursor materials, such as para-aminobenzoic acids, isophthalic acids, tricarboxylic acids, carboxylic groups, sulfonylic groups, phosphates, oligomers, polymers, and isomers thereof, for example.

If black is used, the black pigment can be any commercially available black pigment that provides acceptable optical density and print characteristics. Such black pigments can be manufactured by a variety of known methods such as channel methods, contact methods, furnace methods, acetylene methods, or thermal methods, and are commercially available from such vendors as Cabot Corporation, Columbian Chemicals Company, Evonik, Mitsubishi, and E.I. DuPont de Nemours and Company. For example, commercially available carbon black pigments include Color Black FW 200, Color Black FW 2V, Color Black FW1, Color Black FW 18, Color Black FW S160, Color Black FW S170, Printex including 95, 85, 75, 55, 45, 300, 35, 25, 200, 12, and Special Blacks including, 4A, 4, 5, 6, 550, 350, 250; BP1100, BP900, BP800, M1100, M900, M800, Monarch 1400, Monarch 1300, Monarch 1000, Monarch 900, Monarch 880, and Monarch 700; Cab-O-Jet 200 and Cab-O-Jet 300; Raven 2500ultra, Raven 2000, Raven 7000, Raven 5750, Raven 5250, Raven 5000, and Raven 3500; 45 B, and combinations thereof.

In addition to black, other pigment colorants can be used, such as cyan, magenta, yellow, blue, orange, green, pink, etc. Suitable organic pigments include, for example, azo pigments including diazo pigments and monoazo pigments, polycyclic pigments (e.g., phthalocyanine pigments such as phthalocyanine blues and phthalocyanine greens, perylene pigments, perynone pigments, anthraquinone pigments, quinacridone pigments, dioxazine pigments, thioindigo pigments, isoindolinone pigments, pyranthrone pigments, and quinophthalone pigments), insoluble dye chelates (e.g., basic dye type chelates and acidic dye type chelate), nitropigments, nitroso pigments, anthanthrone pigments such as PR168, and the like. Representative examples of phthalocyanine blues and greens include copper phthalocyanine blue, copper phthalocyanine green and derivatives thereof (Pigment Blue 15 and Pigment Green 36). Representative examples of quinacridones include Pigment Orange 48, Pigment Orange 49, Pigment Red 122, Pigment Red 192, Pigment Red 202, Pigment Red 206, Pigment Red 209, Pigment Violet 19 and Pigment Violet 42. Representative examples of anthraquinones include Pigment Red 43, Pigment Red 194, Pigment Red 177, Pigment Red 216 and Pigment Red 226. Representative examples of perylenes include Pigment Red 123, Pigment Red 190, Pigment Red 189 and Pigment Red 224. Representative examples of thioindigoids include Pigment Red 86, Pigment Red 87, Pigment Red 198, Pigment Violet 36, and Pigment Violet 38. Representative examples of heterocyclic yellows include Pigment Yellow 1, Pigment Yellow 12, Pigment Yellow 13, Pigment Yellow 14, Pigment Yellow 17, Pigment Yellow 73, Pigment Yellow 90, Pigment Yellow 110, Pigment Yellow 117, Pigment Yellow 120, Pigment Yellow 128, Pigment Yellow 138, Pigment Yellow 150, Pigment Yellow 151, Pigment Yellow 155, and Pigment Yellow 213. Such pigments are commercially available in powder, press cake or dispersion form from a number of sources.

The pigments can have a particle size ranging from about 5 nm to about 10 µm; in some examples, the pigments can have a particle size ranging from 10 nm to about 500 nm, although sizes outside this range can be used if the pigment can remain dispersed and provide adequate printing properties.

Ink compositions can also contain dyes as colorants. Examples of dyes suitable for use in the preparation of the ink composition include, but are not limited to, the yellow dyes such as C.I. Yellow 19 (C.I. 13900A), C.I. Yellow 21 (C.I. 18690), C.I. Yellow 61, C.I. Yellow 80, FD&C Yellow #5, and the like, the orange dyes such as C.I. Orange 1 (C.I. 11920), C.I. Orange 37, and the like, red dyes such as C.I. Solvent Red 8, C.I. Red 81, C.I. Solvent Red 82, and the like, pink dyes such as Diaresin Pink M (Mitsubishi Chemical Industries, Ltd.), and the like, violet dyes such as C.I. Solvent Violet 8, and the like, blue dyes such as C.I. Solvent Blue 2, C.I. Solvent Blue 11, and the like, black dyes such as C.I. Solvent Black 3, Acid Black 123, and the like. Some of the pigments and dyes are commercially available in convenient dispersions and may be used in the preparation of the ink composition according to embodiments of the present disclosure.

As used herein, "liquid vehicle" is defined to include any liquid composition that is used to carry colorants, including pigments, to a substrate. A wide variety of liquid vehicle components may be used herein. Such liquid vehicle may include a mixture of a variety of different agents, including without limitation, other surfactants, solvent and co-solvents, buffers, biocides, viscosity modifiers and water. In some examples, the liquid vehicle is an inkjet liquid vehicle.

Organic solvents can be part of the liquid vehicle. Organic solvents are often used to increase the solubility or the dispersibility of the resin or of the colorant that might be present in the composition. Any suitable organic solvents can be used. Examples of suitable classes of organic solvents include polar solvents such as amides, esters, ketones, lactones and ethers. Examples of organic solvents also include N-methylpyrrolidone (NMP), dimethyl sulfoxide, sulfolane, and glycol ethers. In some examples, the solvent is 2-pyrrolidone or a derivative of 2-pyrrolidone, such as 1-(2 hydroxyethyl)-2-pyrrolidone. In some other examples, the liquid vehicle includes a plurality of solvents.

The solvent can be used in an amount representing from about 0.1 to about 30 weight percentage of the ink composition or can be used in an amount representing from about 8 to about 25 weight percentage of the ink composition.

The ink composition can include water. Such water can be used as the ink carrier for the composition and can be part of the liquid vehicle. The water can make up the balance of the ink composition, and may be present in an amount representing from about 40 to about 90 weight percentage, or may be present in an amount representing from about 50 to about 80 weight percentage by weight of the total composition. In order to prevent the clogging of inkjet tip by dissolved salts in the water, deionized water may be used in the preparation of the ink composition.

In addition to water, various types of agents may be employed in the ink composition to optimize the properties of the ink composition for specific applications. The ink composition may also include any number of buffering agents and/or biocides. Any number of commonly known buffers may be used to establish a desired pH level in the ink system. Additionally, various biocides can be used to inhibit growth of undesirable microorganisms. Several examples of suitable biocides include, but are in no way limited to, benzoate salts, sorbate salts, commercial products such as Nuosept® (ISP), Ucarcide® (Dow), Vancide® (RT Vanderbilt Co.), and Proxel® (Avecia), Kordek® MLX (Rohm and Haas) and other known biocides. Such biocides may be contained in amount representing less than about 5 weight percentage of the ink composition. In some examples, biocides represent from about 0.05 to about 2 weight percentage of the ink composition.

Surfactants can also be used and may include standard water-soluble surfactants such as alkyl polyethylene oxides, alkyl phenyl polyethylene oxides, polyethylene oxide (PEO) block copolymers, acetylenic PEO, PEO esters, PEO amines, PEO amides, dimethicone copolyols, ethoxylated surfactants, fluorosurfactants, and mixtures thereof. In some examples, fluorosurfactants or ethoxylated surfactants can be used as surfactants. If used, the surfactant can be present at from about 0.001 to about 10 weight percentage, and, in some examples, can be present at from about 0.001 to about 0.1 weight percentage of the ink composition.

The ink composition can also contain latexes. Latexes include both latex particulates as well as the aqueous medium in which the latex particulates are dispersed. Latex is a liquid suspension including a liquid (such as water and/or other liquids) and polymeric particulates from about 20 nm to about 500 nm in size. As an example, the polymeric particulate can be present in the liquid at from about 0.5 to about 20 weight percentage. Such polymeric particulates can contain a plurality of monomers that are often randomly polymerized, and can be crosslinked. Any latex polymer commercially available can be used in the ink composition including self-dispersed and functionalized latex polymers. Latex polymers can be prepared using any of a number of known emulsion polymerization techniques where co-monomers are dispersed and polymerized in a discontinuous phase of an emulsion. Monomers that can be used include ethyl acrylate or methacrylate; benzyl acrylate; benzyl methacrylate; propyl acrylate; propyl methacrylate;

butyl acrylate; butyl methacrylate; hexyl acrylate; hexyl methacrylate; octadecyl methacrylate or acrylate; lauryl methacrylate or acrylate; hydroxyethyl acrylate or methacrylate; hydroxyhexyl acrylate or methacrylate; vinyl ethyl ketone; vinyl propyl ketone; vinyl hexyl ketone; vinyl octyl ketone; vinyl butyl ketone; cyclohexyl acrylate; methoxysilane; trifluoromethyl styrene; trifluoromethyl acrylate; trifluoromethyl methacrylate; iso-butyl acrylate; iso-butyl methacrylate; 2-ethylhexyl acrylate; 2-ethylhexyl methacrylate; iso-octyl acrylate; iso-octyl methacrylate etc. . . .

In some examples, the ink composition that contains an ink vehicle, from about 0.1 to about 10 weight percentage of colorants, and from about 0.01 to about 10 weight percentage of anti-kogation components that are a mixture of mono-ester and di-ester having the formula (I) and/or the formula (II):

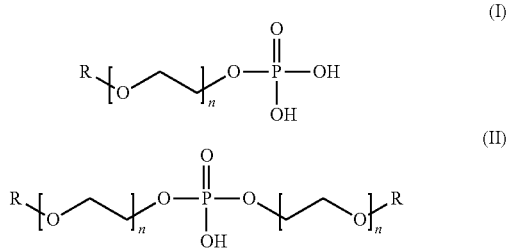

wherein R is an alkyl group having from 1 to 10 carbon atoms and n is an integer ranging from 3 to 10, can be used in a method of forming printed images on substrate in a heated environment. The method includes projecting a stream of droplets of the ink composition onto a media substrate to form the desired printed image. The inkjet ink composition may be established on the substrate via any suitable inkjet printing techniques. Non-limitative examples of such inkjet printing techniques include thermal, acoustic, and piezoelectric inkjet printing. In some examples, the ink compositions such as described herein are utilized in thermal inkjet printers.

The images can be printed on porous and on non-porous substrates, in some examples on porous substrates, using the ink composition described herein. In some other examples, the substrate is paper (non-limitative examples of which include plain copy paper or papers having recycled fibers therein) or photo-paper (non-limitative examples of which include polyethylene or polypropylene extruded on one or both sides of paper), and/or combinations thereof. The substrate can have a thickness along substantially the entire length ranging between about 0.025 mm and about 0.5 mm. In some examples, the printed substrate can be any plastic coated media (as used in out-door signage) and tracing media (for architectural drawings). As used herein, "images" refers to marks, signs, symbols, figures, indications, and/or appearances deposited upon a substrate with either visible or an invisible ink composition. Examples of an image can include characters, words, numbers, alpha-numeric symbols, punctuation, text, lines, underlines, highlights, and the like.

In some examples, a method of inkjet printing over a prolonged period of time, includes jetting an inkjet ink onto a media substrate, wherein said inkjet ink includes: an ink vehicle, from about 0.1 to about 10 weight percentage of colorants, and from about 0.01 to about 10 weight percentage of anti-kogation components that are a mixture of mono-ester and di-ester having the formula (I) and/or the formula (II):

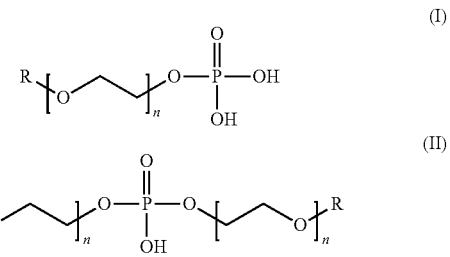

wherein R is an alkyl group having from 1 to 10 carbon atoms and n is an integer ranging from 3 to 10. In some examples, the anti-kogation components designate a mixture of mono-ester and di-ester having the formula (I) and/or the formula (II) wherein R is —(CH$_2$)$_3$CH$_3$ and wherein n is 3.

A method of prolonging the service life of the inkjet printhead includes discharging ink from an orifice wherein the ink contains an ink vehicle, from about 0.1 to about 10 weight percentage of colorants, from about 0.01 to about 10 weight percentage of anti-kogation components that are a mixture of mono-ester and di-ester having the formula (I) and/or the formula (II):

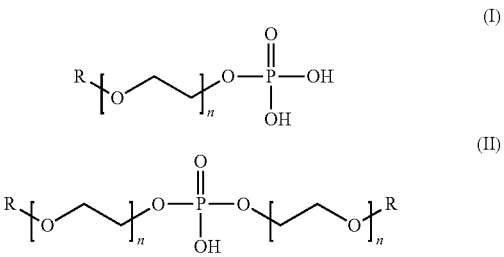

wherein R is an alkyl group having from 1 to 10 carbon atoms and n is an integer ranging from 3 to 10.

The introduction of anti-kogation agents such as disclosed herein, in ink composition, reduces kogation phenomenon of resistors and, in addition, ameliorates or even substantially eliminates clogging phenomenon that can happen in internal ink channels, in firing chambers or in nozzles of printheads. The use of such ink compositions extends thus the life of inkjet pens in general (and particularly thermal inkjet pens) which carry such inks.

The following examples illustrate some embodiments of the disclosure that are presently best known. However, it is to be understood that the following are only illustrative of the application of the principles of the present invention.

EXAMPLE 1

The anti-kogation agent (compound I) having the formula (I) and/or (II) wherein R is C$_2$H$_5$ and n is 3, is synthesized. The 2-[2-(2-ethoxyethoxy)ethoxy]ethyl phosphate is prepared by reaction of polyphosphoric acid with pure solvent triethylene glycol monoethyl ether. A 6.09 g. portion of polyphosphoric acid and 10.67 g. of triethylene glycol monoethyl ether (99% solvent) is combined and heated to 76° C. for 21 hours while mixing with a magnetic stirrer. A 0.30 g. portion of water is added and the mixture is heated further at 76° C. for additional 24 hours. A portion of the reaction mixture is then diluted in water and desalted with semi-preparative HPLC. A 5.49 g. portion of said reaction mixture is then dissolved in water (27.49 g total) yielding to a solution of 200 mg/g. A total of 81 injections of 300 μL each are made onto a 9.4×250 mm, 5 μm Zorbax®XDB-C8 semi-prep HPLC column under the following conditions: column temperature 40° C.; flow rate 3.6 mL/min, with the following gradient conditions: Aq.=20 mM Formic Acid in water; Org=methanol, at 0.0 min—10% Org, at 3.5 min—10.0% Org, at 4.0 min—98.0% Org, at 12.0 min—98.0% Org. The post-run re-equilibration time is 6.0 min. The product is isolated by collecting the column effluent from 5.80 min to 9.00 min. The collected fractions are combined in a round bottom flask and are evaporated to dryness with a rotary vacuum evaporator yielding 3.58 g of a pale yellow oily residue. Analysis of the isolated product indicates that it contains 89% of the mono ester of phosphate and 11% of the diester of phosphate.

The anti-kogation agent (compound III) having the formula (I) and/or (II), wherein R is $C_4H_9$ and n is 3, is synthesized. The 2-[2-(2-butoxyethoxy)ethoxy]ethyl phosphate is prepared by reaction of polyphosphoric acid with pure solvent triethylene glycol mono-butyl ether. A 7.06 g. portion of polyphosphoric acid and 22.24 g. of triethylene glycol mono-n-butyl ether (99% pure solvent) are combined and heated to 90° C. for 20 hours while mixing with a magnetic stirrer. A 9.87 g. portion of the crude reaction mixture is further purified with an acid base extraction to remove residual free alcohol and phosphoric acid. A 9.87 g. portion of said mixture is diluted with 50 mL of water and 70 mL of 1M sodium hydroxide bringing the pH to 12. The aqueous solution is placed into a separatory funnel and extracted with 100 mL of dichloromethane. After shaking the two phases they are allowed to separate overnight. The dichloromethane layer, containing the excess alcohol, hydrophobic impurities, and most of the color, is discarded. The aqueous solution in the separatory funnel is acidified with the addition of 40 mL of 4 M hydrochloric acid. A 10.08 g. portion of sodium chloride is added and dissolved to increase the ionic strength and improve extraction yields. The solution is then extracted seven times with 100 mL portions of dichloromethane combining all of the recovered dichloromethane extracts. The dichloromethane is then evaporated to dryness with a rotary vacuum evaporator yielding 4.66 g of a light yellow oily residue. Analysis of the isolated product indicated that it contains 75% of the mono ester of phosphate and 25% of the diester of phosphate.

Several anti-kogation agent (I, II, III, IV and V) are synthesized according to processes such as described above. The formula of each anti-kogation agent is illustrated in the TABLE 1 below. Component VI is Crodafos®N3A available from Croda Inc. Component VII is Crodafos®N10A available from Croda Inc.

TABLE 1

| Anti-kogation agent | R = | n = |
|---|---|---|
| compound I | C2 | fixed (3) |
| compound II | C2 | fixed (3) |
| compound III | C4 | fixed (3) |
| compound IV | C18 | distribution (about 5) |
| compound V | C18 | More than 3 |
| compound VI | C18 | distribution |
| compound VII | C18 | distribution |

EXAMPLE 2

Ink compositions A to H are prepared in accordance with TABLE 2 as follows. All numbers represent the weight percentage of each components by total weight of the ink composition. The anti-kogation agents, such as described in example 1, are used in ink compositions A to G Ink formulation H is a comparative ink formulation that does not contain any anti-kogation agent.

TABLE 2

| Formulations: | A | B | C | D | E | F | G | H |
|---|---|---|---|---|---|---|---|---|
| compound I | 1.00 | — | — | — | — | — | — | — |
| compound II | — | 1.00 | — | — | — | — | — | — |
| compound III | — | — | 1.00 | — | — | — | — | — |
| compound IV | — | — | — | 1.00 | — | — | — | — |
| compound V | — | — | — | — | 1.00 | — | — | — |
| compound VI | — | — | — | — | — | 1.00 | — | — |
| compound VII | — | — | — | — | — | — | 1.00 | — |
| 1-(2 hydroxy-ethyl)-2-pyrrolidone | 8.00 | 8.00 | 8.00 | 8.00 | 8.00 | 8.00 | 8.00 | 8.00 |
| 2-pyrrolidone | 7.00 | 7.00 | 7.00 | 7.00 | 7.00 | 7.00 | 7.00 | 7.00 |
| 1,6-Hexanediol | 3.00 | 3.00 | 3.00 | 3.00 | 3.00 | 3.00 | 3.00 | 3.00 |
| Tetraethylene Glycol | 3.00 | 3.00 | 3.00 | 3.00 | 3.00 | 3.00 | 3.00 | 3.00 |
| Liponic® EG-1 | 2.00 | 2.00 | 2.00 | 2.00 | 2.00 | 2.00 | 2.00 | 2.00 |
| Surfynol® SEF | 1.10 | 1.10 | 1.10 | 1.10 | 1.10 | 1.10 | 1.10 | 1.10 |
| Proxel® GXL | 0.10 | 0.10 | 0.10 | 0.10 | 0.10 | 0.10 | 0.10 | 0.10 |
| Kordek® MLX | 0.14 | 0.14 | 0.14 | 0.14 | 0.14 | 0.14 | 0.14 | 0.14 |
| Joncryl® 683 (K salt) | 2.00 | 2.00 | 2.00 | 2.00 | 2.00 | 2.00 | 2.00 | 2.00 |
| Magenta colorant | 3.00 | 3.00 | 3.00 | 3.00 | 3.00 | 3.00 | 3.00 | 3.00 |
| water | Up to 100 | Up to 100 | Up to 100 | Up to 100 | Up to 100 | Up to 100 | Up to 100 | Up to 100 |

Surfynol® SEF is a surfactant available from Air Products. Joncryl® 683 is an acrylic resin is available from Johnson Wax. Proxel® GXL is a Biocide available from Zeneca. Crodafos® N-3 acid is available from Croda Inc. Liponic® EG-1 is a surfactant available from Dow Corning. Kordek® MLX is a biocide available from Rohm and Haas. Dissolvine® EDG and Dissolvine®45 S are available from AkzoNobel Corp. Trilon® M is available from BASF Corp.

EXAMPLE 3 a—Kogation Performances

Ink compositions are evaluated for their efficacy in reducing kogation Ink formulations A to H are loaded into 3 different thermal inkjet architectures and fired initially for baseline readings related to steady state drop weight. Each ink composition is printed through its respective print architecture at 1000 million drops per nozzle (MDPN). The nozzle size is of about 20 μm. The kogation performance is determined by measuring the drop weight retained after significant volume of ink firing. The kogation test is carried out with multiple repeating pens for average result. The drop weight data are collected at 2, 4, 6, 8, 10, 20, 50, 60, 70, 80, 90 and 100 MNDP. The drop weight change is determined for each of ink compositions A to H and is expressed in percentage (% DW change) over 100 million drops/nozzle. The results are expressed in TABLE 3 below.

TABLE 3

| Ink compositions | % Drop Weight change | Kogation performances |
|---|---|---|
| A | 21 | Bad |
| B | 25 | Bad |
| C | 10 | Good |

TABLE 3-continued

| Ink compositions | % Drop Weight change | Kogation performances |
| --- | --- | --- |
| D | 3 | Good |
| E | 13 | medium |
| F | 7 | Good |
| G | 0 | Good |
| H | 55 | Bad | b—Filterability Performances

Ink formulations A to H of TABLE 2 are analyzed for their filterability features. The filterability performance represents the anti-clogging benefit of the ink compositions, i.e. the ability of not clogging nozzles and filters present in the printhead.

The filtration time of the ink composition is evaluated by putting 15 g of each ink trough 1 μm pore size filter. The ink composition is then spiked with a metal-salt solution ($Ca^{2+}$). Such addition of calcium will create varying amounts of precipitate that can clog the filter. The filterability performances being linked with the tendency of ink to clog, the lower the filter time is, the better the anti-clogging effect is. The results are summarized in TABLE 4 below. TABLE 4 represents the time (in seconds) needed to filter 15 grams of ink

TABLE 4

| [$Ca^{2+}$] in ppm | Ink composition | | | | | | | |
| --- | --- | --- | --- | --- | --- | --- | --- | --- |
| | A | B | C | D | E | F | G | H |
| 0 | 10 | 17 | 27 | 180 | 180 | 180 | 12 | 9 |
| 4 | — | — | — | — | — | — | 180 | — |
| 30 | 18 | 10 | 11 | — | — | — | — | 9 |
| 60 | 11 | 9 | 10 | — | — | — | — | 10 |
| Filterability performances | Good | Good | Good | Bad | Bad | Bad | Bad | Good |

The invention claimed is:

1. An anti-kogation agent having the formula (I) or (II):

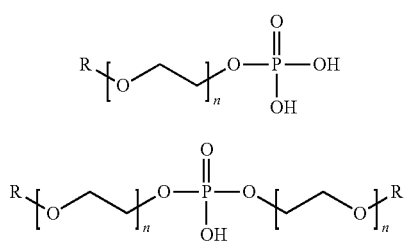

wherein R is —$(CH_2)_3CH_3$ and n is 3.

2. An ink composition comprising:
a. an ink vehicle,
b. from about 0.1 to about 10 weight percentage of colorants,
c. from about 0.01 to about 10 weight percentage of an anti-kogation agent, wherein said anti-kogation agent is selected from a compound having the formula (I), a compound having the formula (II), and mixtures thereof:

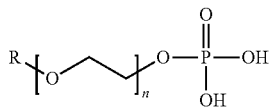

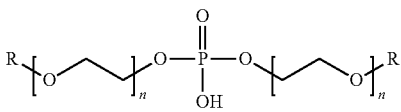

and wherein R is a linear unsubstituted alkyl group having from 1 to 8 carbon atoms and n is an integer ranging from 3 to 7.

3. The ink composition according to claim 2 wherein R is a linear unsubstituted alkyl group having 1, 2, 3 or 4 carbon atoms and n is 3 or 4.

4. The ink composition according to claim 2 wherein R is —$(CH_2)_3CH_3$ and n is 3.

5. The ink composition according to claim 2 wherein anti-kogation agent is present in an amount representing from about 0.2 to about 3 weight percentage of the ink composition.

6. The ink composition according to claim 2 wherein the colorant is present in an amount representing from about 1 to about 6 weight percentage of the ink composition.

7. The ink composition according to claim 2 wherein the colorant is a pigment.

8. The ink composition according to claim 2 wherein the ink composition further comprises latexes.

9. A method to produce the anti-kogation agent of claim 1 that comprises reacting triethylene glycol mono butyl ether with poly-phosphoric acid or phosphoryl chloride ($POCl_3$).

10. A method of forming printed images onto a media substrate comprising projecting a stream of droplets of ink composition, said ink composition containing an inkjet vehicle, from about 0.1 to about 10 weight percentage of colorants, and from about 0.01 to about 10 weight percentage of an anti-kogation agent, said anti-kogation agent being selected from a compound having the formula (I), a compound having the formula (II), and mixtures thereof:

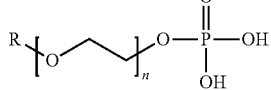

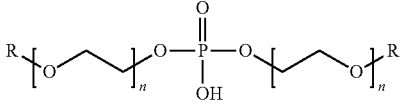

and wherein R is a linear unsubstituted alkyl group having from 1 to 8 carbon atoms and n is an integer ranging from 3 to 7.

11. The method of forming printed images onto a media substrate according to claim 10 wherein the ink composition is established on a media substrate via thermal inkjet printers.

12. The ink composition according to claim 2, wherein the anti-kogation agent is a mixture of 70-90 weight percent of the compound having Formula (I) and 10-30 weight percent of the compound having Formula (II).

* * * * *